(12) United States Patent
Gunawan

(10) Patent No.: US 6,679,866 B1
(45) Date of Patent: Jan. 20, 2004

(54) DEVICE FOR FIRMLY ATTACHING HUMAN-WASTE-COLLECTION BAGS TO THE ABDOMEN BY USING SUCTION RING(S)

(76) Inventor: Andreas Gunawan, 13021 96th. Pl. NE., Kirkland, WA (US) 98034

( * ) Notice: Subject to any disclaimer, the term of this patent is extended or adjusted under 35 U.S.C. 154(b) by 0 days.

(21) Appl. No.: 09/483,540

(22) Filed: Jan. 14, 2000

(51) Int. Cl.[7] .................................................. A61F 5/44
(52) U.S. Cl. ....................... 604/338; 604/339; 604/342; 604/332; 604/345
(58) Field of Search ............................... 604/331, 332, 604/334, 335, 336, 337, 338, 339, 341, 342, 345, 327, 326, 322

(56) References Cited

U.S. PATENT DOCUMENTS

| | | | |
|---|---|---|---|
| 4,419,100 A | * 12/1983 | Alexander | 604/339 |
| 4,460,363 A | * 7/1984 | Steer et al. | 604/336 |
| 4,596,566 A | * 6/1986 | Kay | 604/343 |
| 5,125,917 A | * 6/1992 | Whealin | 604/340 |

* cited by examiner

Primary Examiner—Long V. Le
Assistant Examiner—Ann Y. Lam

(57) ABSTRACT

A device for firmly attaching human-waste-collection bags to the abdomen by using suction rings instead of adhesives. This device comprises of a cap (10) with suction rings, a round plastic sheet (11), a plastic bag (15), and a belt holder(14). A round body (12) of rigid material is used to sandwich the plastic sheet and bag by using the cap (10) at its front end. This device also has a belt holder (14) with a center hole (28) that fits on the rear ring surface (26) of the body (12). This belt holder is equipped with a regular elastic belt for pressing the overall devise firmly against the abdomen.

4 Claims, 6 Drawing Sheets

DEVICE FOR FIRMLY ATTACHING HUMAN-WASTE-COLLECTION BAGS TO THE ABDOMEN BY USING SUCTION RING(S)

CROSS REFERENCE TO RELATED APPLICATIONS

Not applicable.

BACKGROUND

1. Field of Invention

This invention relates to devices used to attach human-waste-collection bags to the abdomen, which are required for people having colostomy or ileostomy due to colon, rectum, or ileos cancer.

2. Description of Prior Art

Presently similar devices available in the market, called colostomy bags, normally use an adhesive substance to attach it to the abdomen. There are two kinds of colostomy bags that use adhesives. One uses an adhesive pad, which is permanently fixed to the bag. This adhesive pad is thrown away together with the bag after its use. Another kind is where the adhesive pad is separated from the bag. The adhesive pad is fixed to the abdomen for about four to six days. This pad is equipped with a snap-on ring. The bag itself is also fitted with a snap-on ring, which fits the ring on the pad. The bag itself can be of the single use type or drainable/washable.

One disadvantage of using adhesive substances is that the adhesive substance is causing irritation to the human skin. This is due to the blocking of the pores of the skin. The prolonged and continues skin irritation causes painful skin rashes, even sores. Until now, people who have had the operation to remove above-mentioned cancers, must suffer and endure the pain due to the rashes and sores.

Another disadvantage of the use of adhesives is that gas accumulated in the bag can not escape. The bags have to be periodically vented to avoid too much pressure. During this venting process, concentrated gas is released into the air and can disturb other people in the vicinity. It also causes embarrassment for the person using the bag.

To overcome these problems, some companies, especially in Germany, have tried to avoid the adhesive. They use a ring that holds the bag and is pressed against the abdomen by a belt. The disadvantage of this method is that the ring frequently slips. While the ring is still being pressed against the abdomen, it does not remain at the same spot. This causes it to slip away from the stoma, and thereby not channel the human waste into the bag. Another problem is that this method also allows the accumulated gas to leak, creating embarrassment for the user.

Attempts to reduce rashes and sores have also been made by the use of skin barriers, which are applied to the skin before the adhesive pads are applied. However, this has not worked well, mainly since this skin barrier itself reduces the adhesive properties of the adhesive and therefor causes the pad to get loose.

Since 1977 the US PTO has granted 83 patents that are related to colostomy bags. However, none of them have designs that even slightly resemble the invention as described below.

SUMMARY

This device comprises a round cap with one or more suction rings, a thin and flexible round sheet of plastic, a plastic bag, a round body, an elastic ring, and a belt holder. A suction ring is defined as a cavity formed by two concentric rings with sufficient space in between them and a backplate.

Objects and Advantages

Objects and advantages of this device are as follows:

(a) This device does not use any adhesive. It therefore prevents cancer patients that have undergone the above-mentioned operations from suffering pain caused by skin rashes and sores. This is a disadvantage of bags using adhesives.

(b) This device uses suction rings, which are formed by incorporating multiple rings in the design of the cap. This prevents the device from slipping away from its intended place on the abdomen. It ensures that all the waste coming out of the stoma will be directed into the bag. Currently available bags that do not use adhesives but use a single ring always slip.

(c) The ability of the belt holder to rotate around the body enables the device to remain in place despite movements.

(d) Another object and advantage is the use of a thin, round, flexible, plastic sheet which will prevent accumulated stomach gas from being released into the air, causing embarrassment for the user. Current devices do not have this sheet.

(e) The above plastic sheet also allows the gas to be very slowly released into the ambient air. It prevents gas accumulation, while still remaining unnoticed by surrounding people. This eliminates the need to vent the bag, which is required for current bags using adhesives.

(f) The above same plastic sheet also prevents contact between human waste and skin, which is another cause of skin rashes. This is also a disadvantage of current bags not using adhesives.

(g) The use of this device is very low in cost since it only requires changing the plastic bag and the plastic sheet. Current bags using adhesives are costly since all parts have to be frequently replaced.

Further objects and advantages will become apparent from the following drawings and descriptions.

DRAWING FIGURES

Following is a description of drawings attached to this application.

FIG. 2A is a perspective view of cap 10.

FIG. 2B is a cross section of cap 10

In both FIGS. 2A and 2B, the important features of the design are numbered as follows:

No. 20 An outer ring.

No. 21 An inner ring.

No. 22 a cap backplate.

No. 23 An inner snap-on ring.

No. 24 A cavity, formed between the outer ring, the cap backplate and the inner ring. This combination functions as the suction ring.

Figure 1:
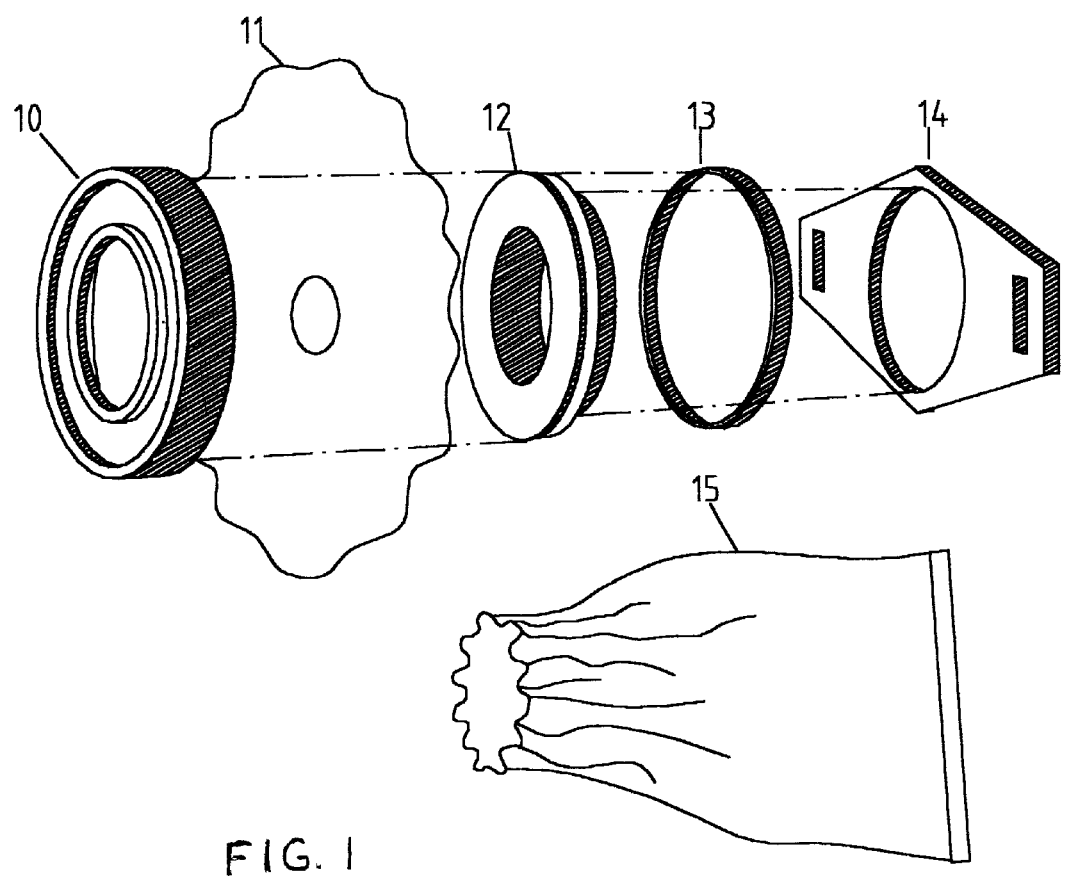
FIG. 1 is an exploded view of the device.
Figure 3:
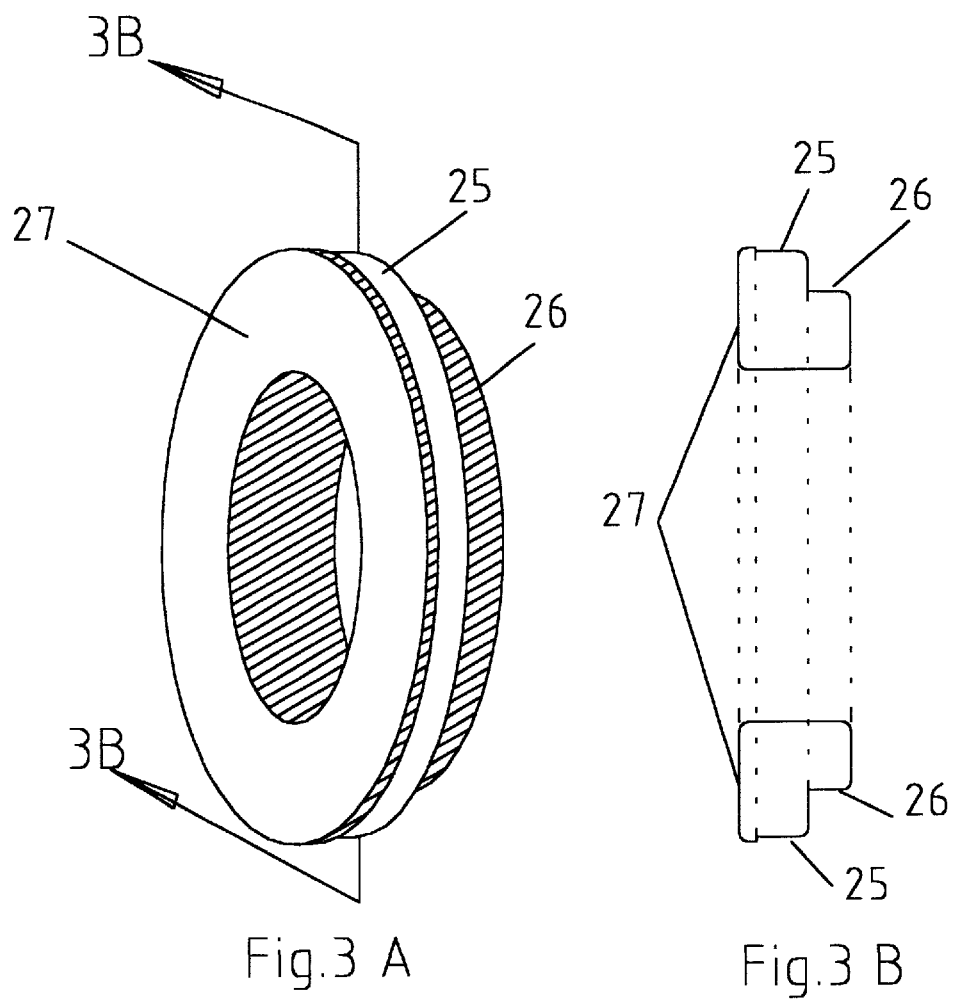

FIG. 3 shows details of the body, as shown in FIG. 1/6 part no.12

FIG. 3A is a perspective view of body 12.

FIG. 3B is a cross section of body 12.

Figure 4:
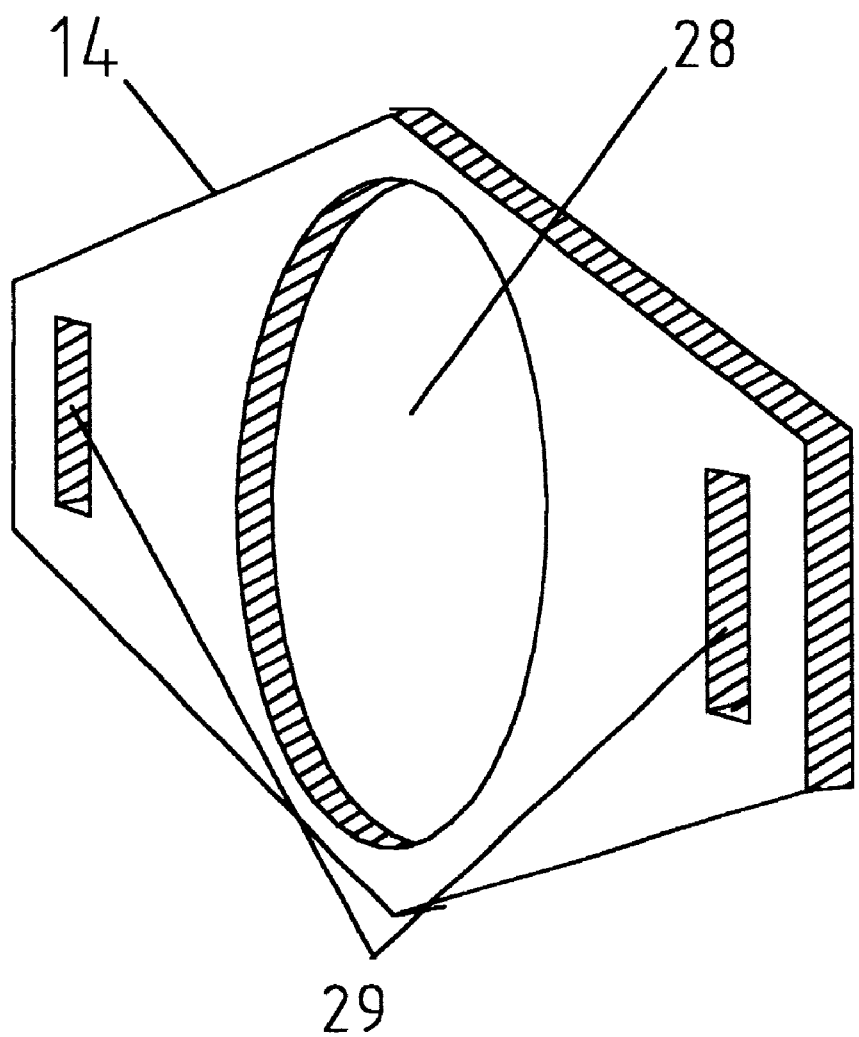

In both FIGS. 3A and 3B the important features are numbered as follows:

No. 25 The center ring surface.
No. 26 The rear ring surface
No. 27 The front surface FIG. 4 shows the belt holder, shown in FIG. 1/6 no 14. In this drawing features are:

No. 28 a center hole.
No. 29 Belt slits.

Figure 5:
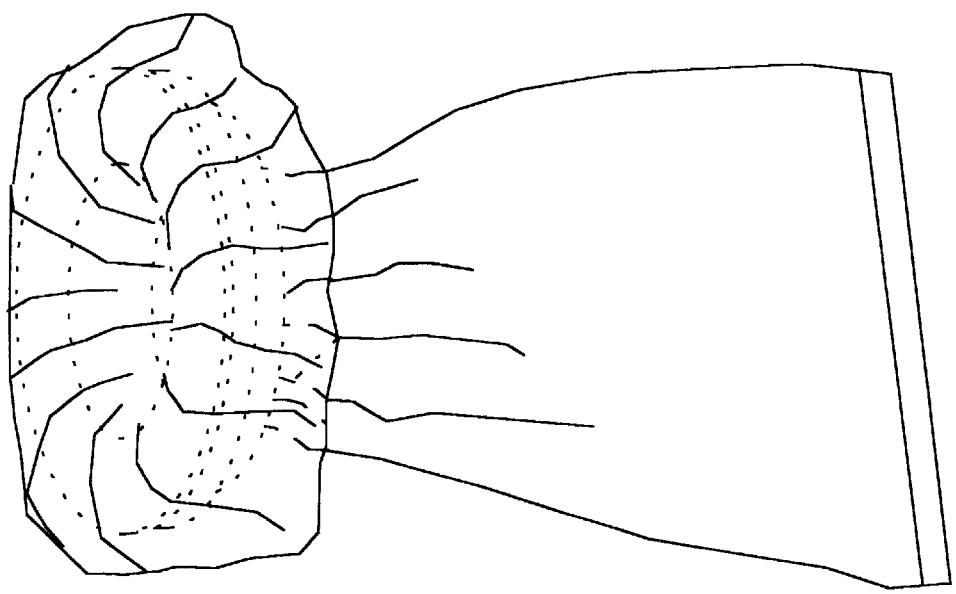

FIG. 5 shows how plastic bag 15 is mounted on body 12.

Figure 6:
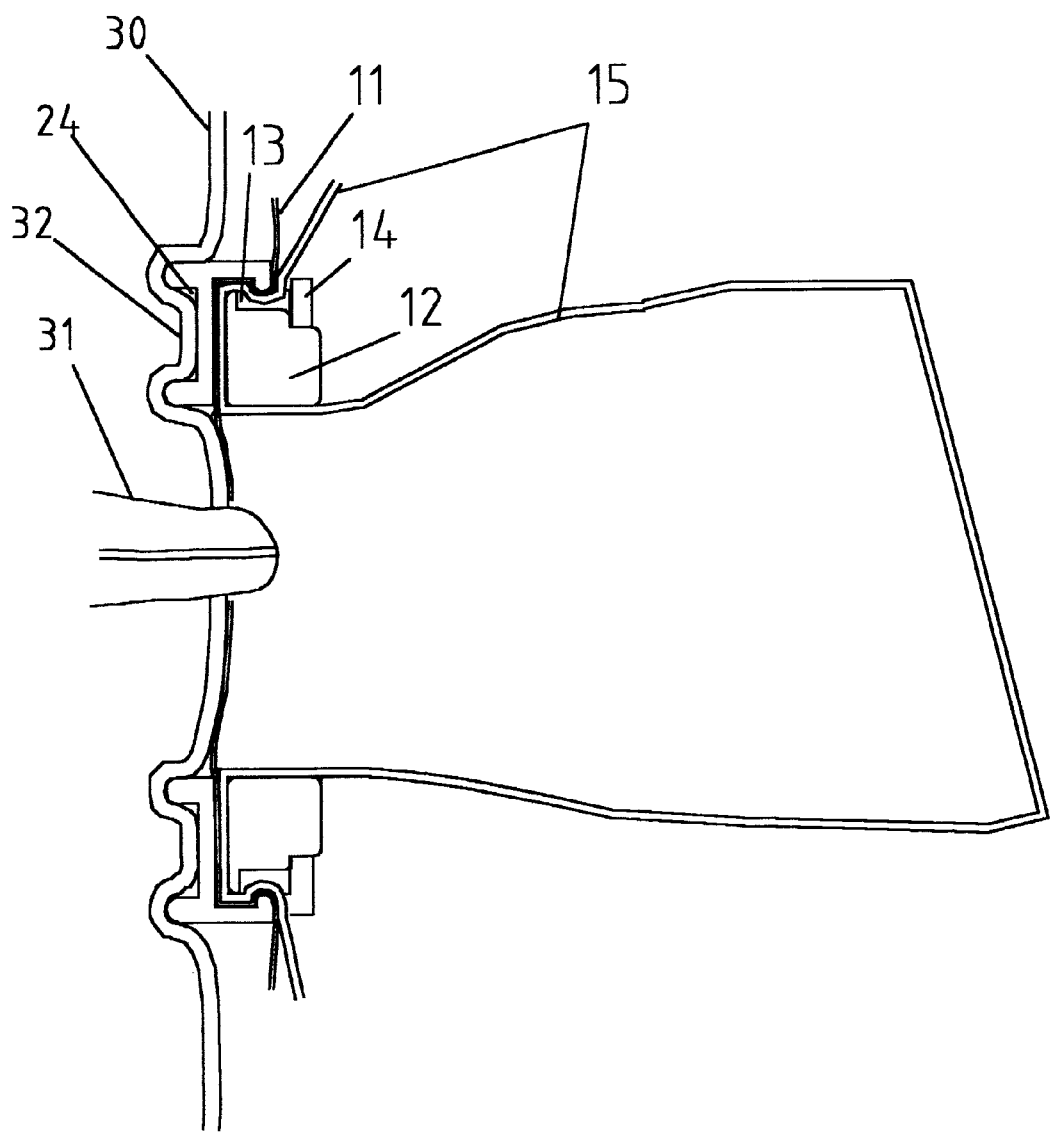

FIG. 6 A schematic view of the device in use.

REFERENCE NUMERALS IN DRAWINGS

10. Cap.
11. Round plastic sheet.
12. Body.
13. Elastic ring.
14. Belt holder.
20. Outer ring incorporated in cap 10.
21. Inner ring incorporated in cap 10.
22. Backplate of cap 10.
23. Snap-on ring of cap 10.
24. Cavity on cap 10.
25. Center ring surface on body 12.
26. Rear ring surface on body 12.
27. Front surface of body 12.
28. Center hole of belt holder.
29. Belt slits of belt holder.
30. Human (abdomen) skin.
31. Stoma.
32. Natural ring from skin.

DESCRIPTION—FIGS. 1 to 6—Preferred Embodiments

Figure 2:
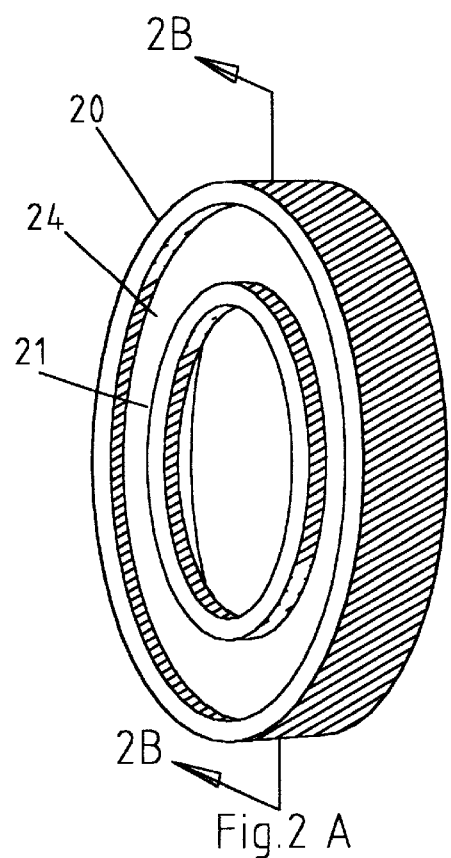
FIG. 2 shows details of a cap, as shown in FIG. 1/6 part no. 10
Figure 2:
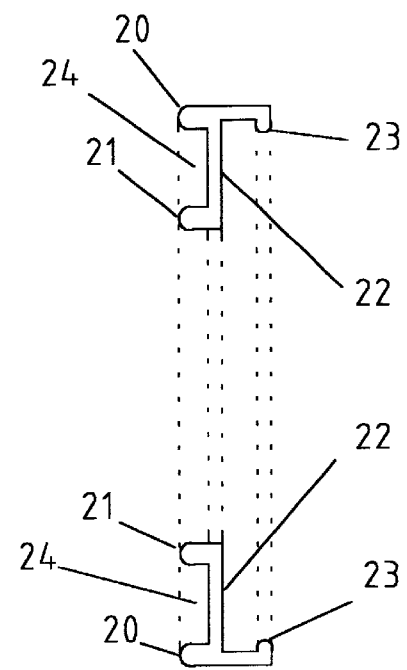

A preferred embodiment of the device is shown in FIG. 1. It is an exploded view of the whole device. The whole device consists of six parts as follows: Part No:

10. A Cap. This is a plastic cap, which has two rings on the front side and a snap-on ring on the inside. It can be made of any plastic material with hardness equivalent to that of low-density polyethylene. Typically, dimensions are as follows: outer ring's diameter is 80 mm, inner ring's diameter is 50 mm, and cap's width is 10 mm. Its full design is shown in FIG. 2.
11. A flexible, thin, round, plastic sheet with a round hole in the middle. Diameter of the plastic sheet is typically 130 mm. The diameter of its hole should be slightly larger then the diameter of the stoma.
12. A round body, made of any material with a minimum density of high-density polyethylene. This body has three different outer ring surfaces: front, center, and rear, and it has a center hole. Its full design is shown in FIG. 3. Dimensions are typically as follows: largest outer diameter is 78 mm, center hole diameter is 50 mm, and its width is 12 mm.
13. An elastic ring that fits on center ring surface 25 of body 12.
14. A belt holder having a center hole with a diameter to fit rear ring surface 26 of body 12 and slits for attaching a regular elastic waist belt. Details are shown in FIG. 4.
15. A regular non-gas-permeable plastic bag.

The above parts fit together as follows:

Elastic ring 13 is mounted on center ring surface 25 of body 12.

Plastic bag 15 is pushed through the center hole of body 12, opened and turned over backwards to cover front surface 27 of body 12. See FIG. 5.

Round plastic sheet 11 is placed against the covered front surface of body 12.

Then cap 10 is pressed against body 12, so that it clips with inner snap-on ring 23 resting on elastic ring 13. So round plastic sheet 11 and the front end of bag 15 are sandwiched between cap 10 and body 12.

The final stage of the assembly is to push the rear end of bag 15 through central opening 28 of belt holder 14, and slide this belt holder right on rear ring surface 26 of body 12.

A schematic view of the assembled device, pressed against the abdomen is shown in FIG. 6.

Alternative Embodiments

Alternative embodiments are:

Provide three or more rings in the design of the front end of cap 10. This will create two or more suction rings and therefore provide more grip to the abdomen skin and further reduce the already small risk of slipping.

Design belt holder 14 to become a fixed part of body 12 instead of moveable as described above.

Operation—FIG. 1

See FIG. 6. The front end of the assembled device is pushed against the abdomen, making sure that the center hole of plastic sheet 11 fits around stoma 31. The diameter of this center hole is slightly larger than the diameter of the stoma. The device is pushed against the skin by a regular elastic belt. This elastic belt has been mounted on belt holder 14 using the provided belt slits 29.

At the front end of cap 10, rings numbered 20 and 21, together with backplate no 22, form a cavity 24. Into this cavity, skin 30 of the abdomen tries to fit.

As the cap is pressed against the skin, it forces the air out of this cavity 24, in effect forming a vacuum. Therefore these two rings, together with the backplate, act as a suction ring. The negative air pressure, which then exists, keeps skin 30 in the cavity forming a natural ring 32 out of human (abdomen) skin. This prevents the whole device from slipping. Slipping is one of the disadvantages of devices that do not use adhesives, but use only one ring.

At the same time, plastic sheet 11 also presses against the skin. It then together with the skin forms a valve. The more gas accumulates in the bag, the more pressure is in the bag. The tighter this plastic sheet is pressed against the skin, the less opportunity there is for the accumulated gas to escape from between the sheet and the skin. The suction ring as explained above will form another barrier against escaping gas. Leaking stomach gas is another disadvantage of adhesiveless devices with using only one ring.

This device, in its usage however, does not completely prevent gas from escaping. In small quantities gas still leaks through the wrinkles formed by the bag and the plastic sheet as they are being pressed between elastic ring 13 and snap-on ring 23 of cap 10. The gas, which escapes in small quantities, is mixed with the outside air. This makes it unnoticeable, and also makes it not necessary to vent the bag, as is required with all colostomy bags using adhesives.

Belt holder 14 fits on rear ring surface 26 of body 12. This allows the belt holder to rotate around this ring. This will make it possible for the whole device to remain stationary relative to the abdomen, even if the person wearing it makes all kinds of movements.

Conclusion, Ramifications, and Scope

From the above, it is clear that this device provides a solution for cancer patients that have had a colostomy or ileostomy and have to endure pain due to skin rashes and/or sores, due to the use of adhesives. This is achieved by the elimination of adhesives, without creating the inherent problems of slipping and leaking. Slipping and leaking is an inherent problem of devices using only one ring. The advantages of this device are:

- The absence of adhesives will eliminate the development of skin rashes and/or sores endured by most people wearing colostomy bags.
- The use of two or more rings at the front end of cap 10 which are pressed against the abdomen skin creates a positive grip which prevents the device from shifting its position relative to the location of the stoma on the abdomen skin. This shifting is an inherent weakness of devices using only one ring. This will ensure the waste to be channeled into the bag.
- The use of a thin flexible round sheet which forms a valve together with the abdomen skin prevents the release of accumulated gas into the air, with the inherent spreading of bad odor which can cause embarrassment. This release of accumulated gas is another weakness of in the market available adhesiveless devices.
- Round plastic sheet 11 also prevents the human waste from coming in contact with the skin, another cause of skin rashes and sores. This contact between human waste and the abdomen skin is a weakness of devices that do not utilize the plastic sheet.
- The very slow leakage through the wrinkles of plastic bag 15 as explained above prevents the accumulation of gas. Therefore this eliminates the requirement to vent the bag, which is needed with devices using adhesives. This leakage will not cause any embarrassment since the small quantities of gas released will not be noticeable.
- This design allows the repeated usage of the device, while only changing plastic bag 15 and round plastic sheet 11. This makes the cost of using the device very low.
- The ability of belt holder 14 to rotate around rear ring surface 26 of body 12 helps the device to remain in place despite of the body movements of the wearer.

While the above description contains detailed specificities, these should not be construed as limitations on the scope of the invention, but rather as exemplification of one preferred embodiment thereof. Many other variations are possible, such as the use of more rings on the front end of the cap, reduced or increased diameter of the device, and the use of a fixed belt holder.

Accordingly, the scope of the invention should be determined not by the embodiment(s) illustrated or explained, but by the appended claims and their legal equivalents.

I claim:

1. A human waste collection device for attaching to an abdomen, comprising:

an annular cap adapted to be pressed around a stoma in said abdomen, wherein said annular cap is comprised of an outer ring and an inner ring on an inner side of said annular cap, and a back plate connected between said outer ring and said inner ring on an outer side of said annular cap;

an annular cavity defined between said outer ring and said inner ring of said annular cap;

an annular round body comprised of a higher density plastic material than said annular cap, wherein said round body is positioned against said back plate of said annular cap on said outer side of said annular cap and is generally coextensive therewith;

a belt holder attached to said round body and adapted to be strapped around a person; and a bag with an open end attached to a center hole of said round body for collecting human waste ejected from said stoma.

2. A human waste collection device for attaching to an abdomen, comprising:

an annular cap adapted to be pressed around a stoma in said abdomen, said annular cap is comprised of an outer ring and an inner ring on an inner side of said annular cap, and a back plate connected between said outer ring and said inner ring on an outer side of said annular cap;

a continuous annular cavity defined between said outer ring and said inner ring of said annular cap, said continuous cavity comprising a continuous annular suction ring for drawing skin into said cavity and preventing slippage;

an annular round body made of a higher density plastic material than said annular cap, said round body is positioned against said outer side of said annular cap and is generally coextensive therewith;

a belt holder attached to said round body and adapted to be strapped around a person;

a bag with an opening attached to a center hole of said round body for collecting human waste ejected from said stoma; and a disposable flexible sheet detachably clamped between said annular cap and said annular round body, said flexible sheet including a hole substantially smaller than a center hole on said annular cap but large enough to encircle said stoma, said flexible sheet is adapted to isolate and protect said skin within said center hole on said annular cap from said human waste collected in said bag.

3. A human waste collection device for attaching to an abdomen, comprising:

an annular cap made of a and adapted to be pressed around a stoma in said abdomen, said annular cap is comprised of an outer ring and an inner ring on an inner side of said annular cap, a back plate connected between said outer ring and said inner ring on an outer side of said annular cap, and a snap-on ring around a circumference of said annular cap on said outer side;

a continuous annular cavity defined between said outer ring and said inner ring of said annular cap, said continuous cavity comprising a continuous annular suction ring for drawing skin into said cavity and preventing slippage;

an annular round body made of a higher density plastic material than said annular cap, said round body is positioned against said outer side of said annular cap and is generally coextensive therewith, said round body is detachably secured within said snap-on ring;

a belt holder attached to said round body and adapted to be strapped around a person;

a disposable bag attached to said annular round body for collecting human waste ejected from said stoma, said bag having an open end inserted through a center hole of said annular round body from an outer side of said annular round body, and detachably clamped between said annular cap and said annular round body;

a disposable flexible sheet detachably clamped between said annular cap and said annular round body inward of said bag, said flexible sheet including a round hole substantially smaller than a center hole on said annular cap but large enough to closely encircle said stoma, said plastic sheet is adapted to isolate and protect said skin within said center hole on said annular cap from said human waste collected in said bag; and wrinkles on said bag and said flexible sheet between said annular cap and said annular round body enabling any gas in said bag to gradually and inconspicuously leak out and thus eliminating the need for sudden venting.

4. The human waste collection device of claim 3, further including an elastic ring squeezed between an outer rim of said annular round body and an inner rim of said snap-on ring to generally seal said bag and said plastic sheet against said snap-on ring.

\* \* \* \* \*